United States Patent
Tan

(10) Patent No.: US 7,193,716 B2
(45) Date of Patent: Mar. 20, 2007

(54) ARRANGEMENT OF COLOR FILTERS FOR CHARACTERIZING THE COLOR OF AN AGGREGATE LIGHT

(75) Inventor: Boon-Keat Tan, Penang (MY)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 275 days.

(21) Appl. No.: 11/001,523

(22) Filed: Dec. 1, 2004

(65) Prior Publication Data

US 2006/0114461 A1    Jun. 1, 2006

(51) Int. Cl.
*G01N 21/25* (2006.01)
*G02B 5/22* (2006.01)

(52) U.S. Cl. .................. 356/406; 359/885; 359/891; 356/419

(58) Field of Classification Search ............. 349/106; 359/885, 891
See application file for complete search history.

(56) References Cited

U.S. PATENT DOCUMENTS

| | | | | |
|---|---|---|---|---|
| 4,463,074 | A * | 7/1984 | Gilmour et al. | 430/7 |
| 4,800,375 | A * | 1/1989 | Silverstein et al. | 345/694 |
| 5,737,042 | A * | 4/1998 | Shinohara et al. | 349/57 |
| 6,023,315 | A * | 2/2000 | Harrold et al. | 349/108 |
| 6,327,008 | B1 * | 12/2001 | Fujiyoshi | 349/106 |
| 6,339,459 | B1 * | 1/2002 | Ichikawa et al. | 349/95 |
| 6,667,819 | B2 * | 12/2003 | Nishikawa et al. | 359/15 |

OTHER PUBLICATIONS

"The Color Fitler Array FAQ", www.fillfactory.com, Mar. 27, 2001, 10 pages.

* cited by examiner

*Primary Examiner*—Gregory J. Toatley, Jr.
*Assistant Examiner*—Bryan Giglio

(57) ABSTRACT

In one embodiment, a plurality of color filters arranged in an N×N array. The color filters comprise equal numbers of color filters for each of three or more different colors. The color filters are arranged symmetrically in both an X and a Y direction. The center of gravity for each set of like-colored filters is the center of the array.

20 Claims, 3 Drawing Sheets

ARRANGEMENT OF COLOR FILTERS FOR CHARACTERIZING THE COLOR OF AN AGGREGATE LIGHT

BACKGROUND

The intensity of an aggregate light (i.e., a light comprised of different wavelengths of light) can be characterized by means of a single intensity measurement acquired by a single photodetector. However, to characterize the color of an aggregate light, one must acquire a plurality of intensity measurements corresponding to the wavelengths (or ranges of wavelengths) that are included in the light.

One way to acquire intensity measurements for different wavelengths of light is to position a translucent wheel comprising different color filters (e.g., red, green and blue color filters) in front of a single photodetector. As the wheel rotates, a series of intensity measurements may then be acquired as the different color filters pass in front of the photodetector.

Another way to acquire intensity measurements for different wavelengths of light is to position different color filters over different photodetectors. The different photodetectors may then be used to acquire different intensity measurements.

SUMMARY OF THE INVENTION

In one embodiment, a plurality of color filters arranged in an N×N array. The color filters comprise equal numbers of color filters for each of three or more different colors. The color filters are arranged symmetrically in both an X and a Y direction. The center of gravity for each set of like-colored filters is the center of the array.

Other embodiments are also disclosed.

BRIEF DESCRIPTION OF THE DRAWINGS

Illustrative and presently preferred embodiments of the invention are illustrated in the drawings, in which.

DETAILED DESCRIPTION OF AN EMBODIMENT

Figure 1:
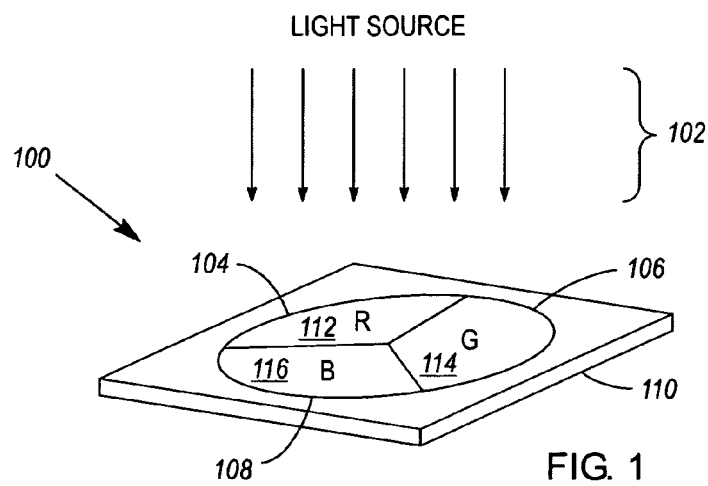
FIG. 1 illustrates an exemplary system for characterizing the color of an aggregate light.

FIG. 1 illustrates a system 100 for characterizing the color of an aggregate light 102. The system 100 is of the type that comprises a plurality of photodetectors 104, 106, 108, each of which measures the intensity of a different wavelength (or range of wavelengths) of light 102. In some cases, the photodetectors 104–108 may take the form of photodiodes or phototransistors.

By way of example, the system 100 comprises three photodetectors 104–108, each of which is formed within a common integrated circuit 110. Alternately, the photodetectors 104–108 could be formed within different integrated circuits.

The system 100 also comprises a plurality of color filters 112, 114, 116. Each color filter 112–116 is positioned above a different one of the photodetectors 104–108, and is preferably formed on one of the photodetectors 104–108 (e.g., by means of lithography). Alternately, the color filters 112–116 may be formed on the translucent surface of a package in which the integrated circuit 110 is mounted; on the surface of a translucent encapsulant that covers the integrated circuit 110; or on the surface of an integrated color filter that is positioned above the integrated circuit 110 (e.g., a filter disc or filter lens). Although the color filters 112–116 are shown to be red (R), green (G) and blue (B) color filters, they could alternately comprise yellow, magenta and cyan color filters, or other collections of three or more differently colored filters.

Figure 2:
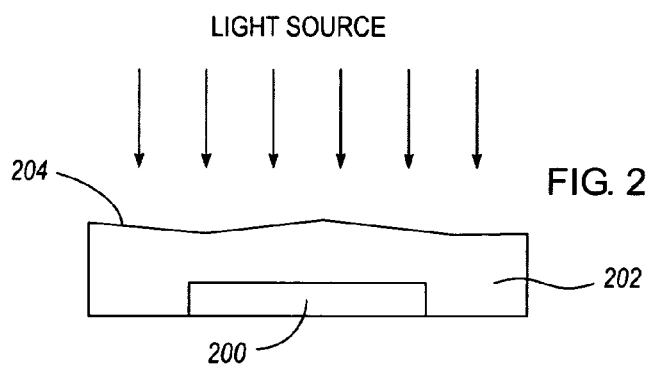
FIG. 2 illustrates an integrated circuit in which a die is wire-bonded to a substrate, and then encapsulated by a translucent material having an irregular light absorption surface.

When the color of an aggregate light 102 is characterized using different photodetectors 104–108, each photodetector 104–108 will necessarily receive a different set of incident light rays. If the aggregate light 102 sensed by the photodetectors 104–108 is well-mixed, and if the photodetectors 104–108 are positioned in close proximity to one another, then each photodetector 104–108 should receive about the same quantity of each wavelength of light. However, such an ideal scenario is rarely achieved. For example, the aggregate light 102 may be non-uniformly mixed, thereby leading to some photodetectors 104–108 receiving more, less or a different mix of light. Or, for example, the photodetectors 104–108 may lie on a plane that is tilted with respect to the source of the aggregate light 102, thereby leading to a light gradient across the surfaces of the photodetectors, which causes some of the photodetectors 104–108 to receive more light than others (as shown in FIG. 1). Additionally, different amounts of light may be absorbed by, or reflected from, different ones of the photodetectors 104–108 as a result of irregularities in any one or more of: the surfaces of the photodetectors 104–108, the surface of a package or encapsulant that covers the photodetectors 104–108, or the surface of a lens or integrated color filter that is positioned above the photodetectors 104–108. By way of example, FIG. 2 illustrates an integrated circuit 200 having photodetectors thereon is encapsulated by a translucent material 202 having an irregular light absorption surface 204. Such an irregular light absorption surface 204 is especially common when an encapsulant 202 is applied over an integrated circuit 200 by means of "dam and fill".

One way to mitigate some or all of the above problems is to expand the system 100 to include more than one photodetector for measuring the intensity of each wavelength of light. In this manner, the intensity measurements generated by photodetectors receiving the same wavelength(s) of light may be aggregated (e.g., summed or averaged) to account for light and manufacturing variances that affect different ones of the photodetectors. An issue then arises as to how the photodetectors and their color filters should be arranged.

Figure 3:
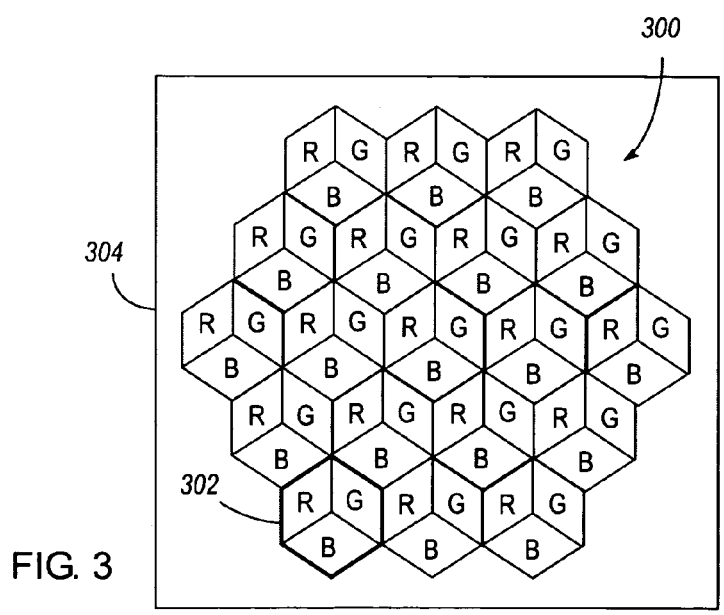
FIG. 3 illustrates a plurality of photodetectors and corresponding color filters arranged in a honeycomb pattern.

One way to arrange a plurality of photodetectors and their corresponding color filters is in a honeycomb pattern 300, as shown in FIG. 3. Each "cell" 302 of the honeycomb 300 includes a plurality of photodetectors, and each photodetector in a common cell 302 is provided with a different color filter (e.g., red (R), green (G) or blue (B)). Although a honeycomb of photodetectors and color filters 300 is reasonably effective at mitigating light gradients and other effects, its irregular shape makes inefficient use of an integrated circuit's surface area 304.

Figure 4:
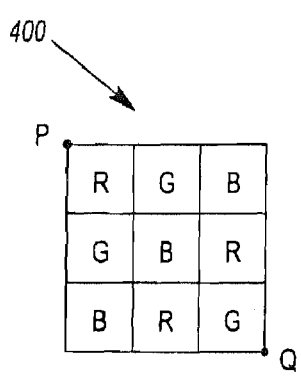
FIG. 4 illustrates a plurality of photodetectors and corresponding color filters arranged in an M×M diagonal-stripe pattern.

Another way to arrange a plurality of photodetectors and their corresponding color filters is in an M×M array 400, as shown in FIG. 4. Within the array 400, the different colored filters may be arranged in a variety of ways, including that of a diagonal-stripe pattern. A diagonal-stripe pattern can be useful in that there are an equal number of color filters for each color, and the distribution of color filters is both horizontally and vertically balanced (i.e., there are an equal number of like-colored filters in each row and column of the array 400). The distribution of color filters is also balanced in one diagonal direction (i.e., along diagonal RBG); however, it is not balanced in the other diagonal direction (i.e., along diagonal BBB). As a result, certain tilts of the color filter plane with respect to a light source can result in a color-weighted collection of photodetectors receiving more or less light. For example, if the color filter plane is tilted such that corner P is closer a light source than corner Q, then a red-filtered photodetector would receive more light, while a green-filtered photodetector would receive less light. As a result, a collection of photodiodes could erroneously report an aggregate light to have too strong of a red component, and too weak of a green component.

Figure 5:
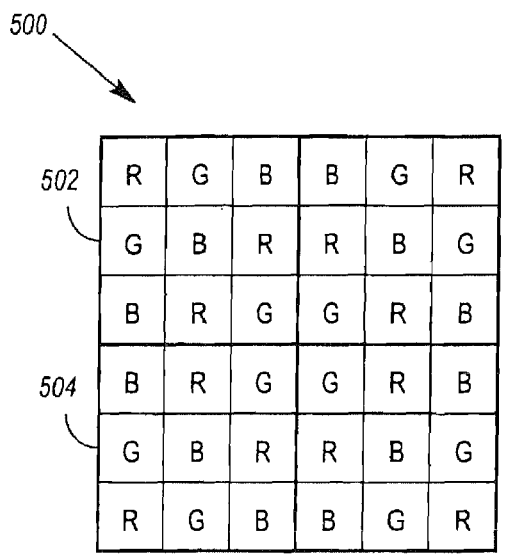
FIG. 5 illustrates a 6×6 balanced color filter structure.
Figure 6:
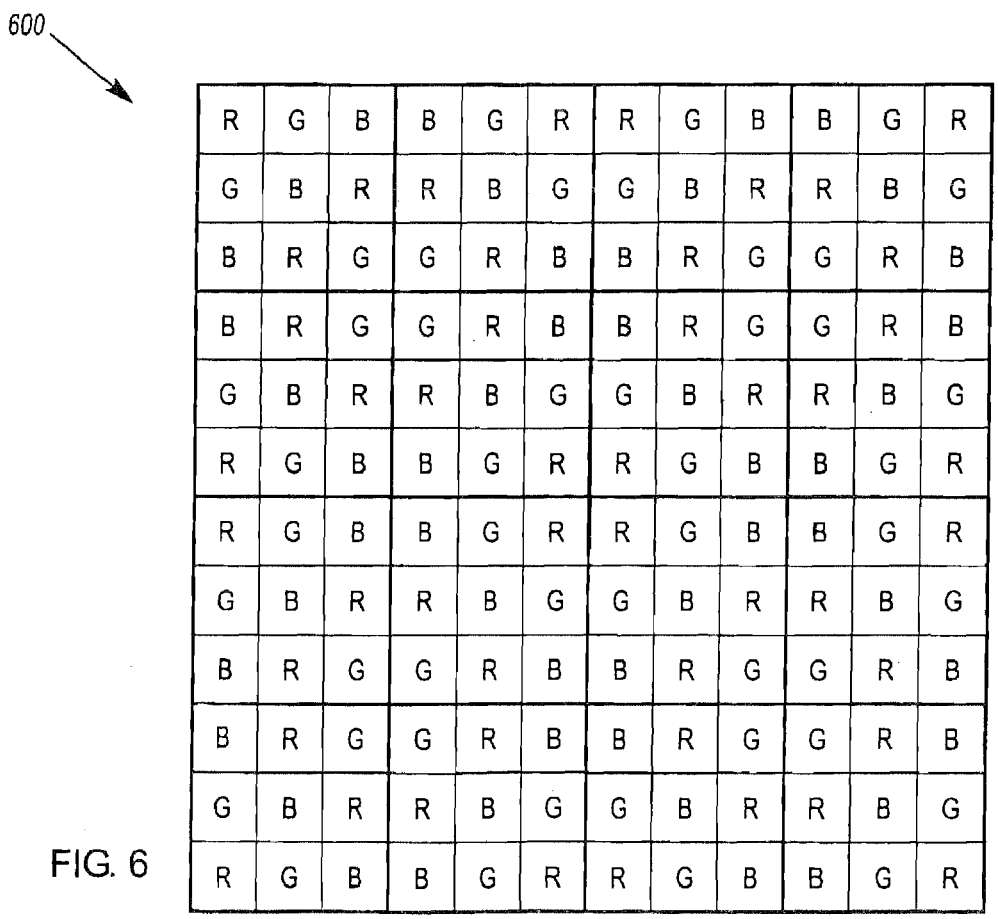
FIG. 6 illustrates a 12×12 balanced color filter structure.

FIGS. 5 & 6 illustrate alternate arrangements of color filters 500, 600. Each arrangement 500, 600 comprises an N×N array of color filters, with equal numbers of color filters for each of three or more different colors. The color filters are not only horizontally and vertically balanced, but are also symmetrically arranged in both an X and Y direction. Further, the center of gravity for each set of like-colored filters is at the center of each array 500, 600. By way of example, the color filters are once again shown to comprise red (R), green (G) and blue (B) color filters.

The arrangement 500 of color filters shown in FIG. 5 may be formed from a plurality of M×M diagonal-stripe patterns 400, with each pair 502, 504 of adjacent diagonal-stripe patterns being mirrored about their common axis. By way of example, FIG. 5 illustrates a 6×6 array of color filters 500 comprised of four, mirrored, 3×3 diagonal-stripe patterns (i.e., M=3, N=6). FIG. 6 illustrates a 12×12 array of color filters 600 comprised of sixteen, mirrored, 3×3 diagonal-stripe patterns (i.e., M=3, N=12).

Figure 7:
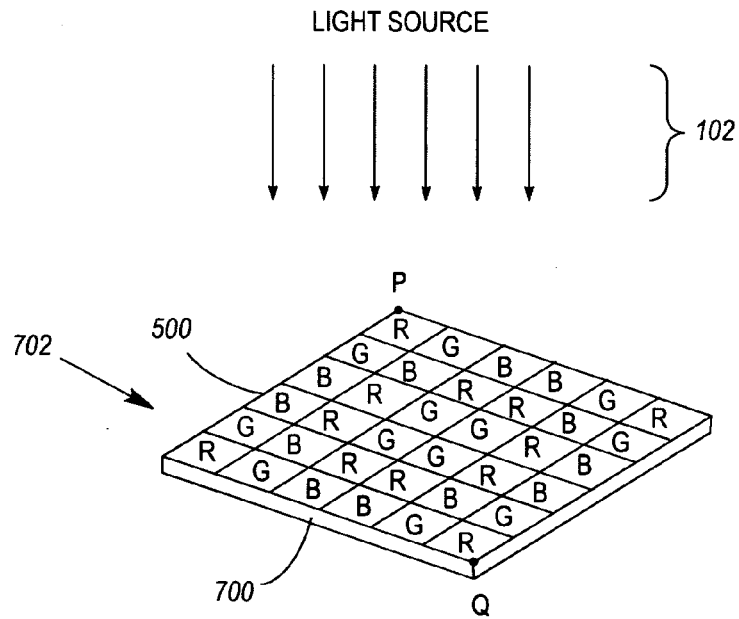
FIG. 7 illustrates an exemplary use of the color filter arrangement shown in FIG. 5.

FIG. 7 illustrates an exemplary use of the color filter arrangement shown in FIG. 5. In FIG. 7, the arrangement of color filters 500 shown in FIG. 5 is applied to an array of photodetectors 700 in a plane that is tilted with respect to the source of an aggregate light 102. As a result, a light gradient appears across the surfaces of the photodetectors 700. This light gradient causes some of the photodetectors (e.g., the photodetectors at corner P) to receive more light, while others receive less (e.g., the photodetectors at corner Q). However, note that the photodetectors appearing at corners P and Q are associated with the same color filters (red (R)). Thus, as one red color filter receives more light, another red filter receives less light. The color filters shown in FIGS. 5–7 are therefore color balanced about all axes.

In one embodiment, a system to aggregate (e.g., sum or average) outputs of photodetectors positioned behind like-colored filters is incorporated into a single integrated circuit 702 along with all of the photodetectors 700. The system may also subject the photodetector outputs to additional (or alternate) analyses. In an alternate embodiment, the outputs of the photodetectors 700 could be routed to an off-chip, hard-wired (e.g., circuit-based) or programmed (software or firmware-based) system for aggregation or analysis.

Figure 8:
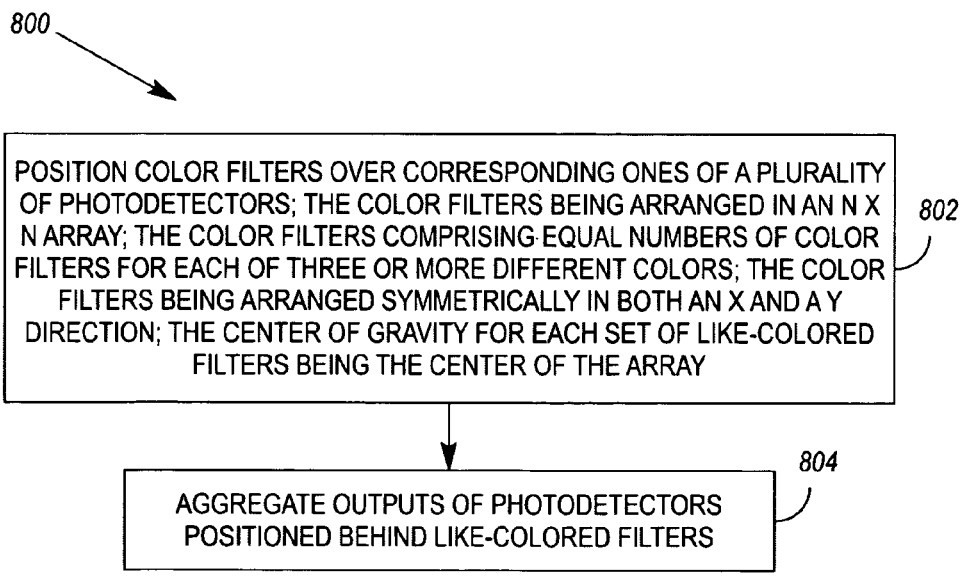
FIG. 8 illustrates an exemplary method for making the color filter arrangements shown in FIGS. 5–7, as well as other color filter arrangements.

FIG. 8 illustrates a method 800 for making the color filter arrangements shown in FIGS. 5–7, as well as other color filter arrangements. The method 800 comprises positioning 802 color filters over corresponding ones of a plurality of photodetectors. The color filters are arranged in an N×N array and comprise equal numbers of color filters for each of three or more different colors. The color filters are further arranged symmetrically, in both an X and a Y direction. The center of gravity for each set of like-colored filters is the center of the array. The method then continues with the aggregation 804 of outputs of photodetectors positioned behind like-colored filters.

The methods and apparatus disclosed in FIGS. 5–8 can be useful in mitigating the effects of photodetector tilt, incorrect photodetector positioning, and differences in light reflection/absorption rates as a result of irregular refraction surfaces through which a light passes. The color filters shown can also be useful in that they conform to a square grid, thereby making them space-efficient.

Note that, although the arrangements of color filters shown in the attached figures are shown to comprise specific arrangements of red (R), green (G) and blue (B) color filters, the primary significance of the arrangements is their patterns of color filters, and not the colors themselves. Thus, for example, red color filters could be swapped with blue color filters, or a different set of color filters could be used, so long as each of the illustrated patterns of color filters is maintained.

What is claimed is:

1. Apparatus, comprising:
a plurality of color filters arranged in an N×N array; the color filters comprising equal numbers of color filters for each of three or more different colors; the color filters being arranged symmetrically in both an X and a Y direction; the center of gravity for each set of like-colored filters being the center of the array.

2. The apparatus of claim 1, wherein subsets of color filters are arranged to form a plurality of M×M diagonal-stripe patterns, with each pair of adjacent diagonal-stripe patterns being mirrored about their common axis.

3. The apparatus of claim 2, wherein each M×M diagonal-stripe pattern is a 3×3 diagonal-stripe pattern.

4. The apparatus of claim 1, wherein the color filters comprise red, green and blue color filters.

5. The apparatus of claim 1, wherein the array is a 6×6 array.

6. The apparatus of claim 1, wherein the array is a 12×12 array.

7. The apparatus of claim 1, further comprising a plurality of photodetectors, wherein said color filters are positioned above corresponding ones of the photodetectors.

8. The apparatus of claim 7, wherein the photodetectors comprise photodiodes.

9. The apparatus of claim 7, wherein the color filters are formed on the photodetectors.

10. The apparatus of claim 7, further comprising a system to aggregate outputs of photodetectors positioned behind like-colored filters.

11. The apparatus of claim 10, wherein the system average the outputs of photodetectors positioned behind like-colored filters.

12. The apparatus of claim 10, wherein the system sums the outputs of photodetectors positioned behind like-colored filters.

13. A method, comprising:
    positioning color filters over corresponding ones of a plurality of photodetectors; the color filters being arranged in an N×N array; the color filters comprising equal numbers of color filters for each of three or more different colors; the color filters being arranged symmetrically in both an X and a Y direction; the center of gravity for each set of like-colored filters being the center of the array; and
    aggregating outputs of photodetectors positioned behind like-colored filters.

14. The method of claim 13, wherein the color filters are formed on corresponding ones of the plurality of photodetectors.

15. The method of claim 13, wherein said aggregation comprises averaging.

16. The method of claim 13, wherein said aggregation comprises summing.

17. The method of claim 13, further comprising, arranging subsets of the color filters to form a plurality of M×M diagonal-stripe patterns, with each pair of adjacent diagonal-stripe patterns being mirrored about their common axis.

18. The method of claim 17, wherein each M×M diagonal-stripe pattern is laid out as a 3×3 diagonal-stripe pattern.

19. The method of claim 13, wherein the color filters comprise red, green and blue color filters.

20. The method of claim 13, further comprising, forming the color filters on the photodetectors.

* * * * *

UNITED STATES PATENT AND TRADEMARK OFFICE
CERTIFICATE OF CORRECTION

PATENT NO. : 7,193,716 B2  Page 1 of 1
APPLICATION NO. : 11/001523
DATED : March 20, 2007
INVENTOR(S) : Boon-Keat Tan It is certified that error appears in the above-identified patent and that said Letters Patent is hereby corrected as shown below:

Col. 2 Line 1 Delete "Fitler" and insert -- Filter --, therefor.

Col. 4 Line 62 In Claim 11, delete "average" and insert -- averages --, therefor.

Signed and Sealed this

Sixteenth Day of December, 2008

JON W. DUDAS
*Director of the United States Patent and Trademark Office*